United States Patent [19]

Radwill

[11] 4,322,981
[45] Apr. 6, 1982

[54] RAILWAY CAR TRUCK FATIGUE DETECTOR

[75] Inventor: Robert P. Radwill, Chicago, Ill.

[73] Assignee: AMSTED Industries Incorporated, Chicago, Ill.

[21] Appl. No.: 167,239

[22] Filed: Jul. 10, 1980

[51] Int. Cl.³ .............................................. G01N 3/32
[52] U.S. Cl. .................................. 73/810; 105/197 R; 116/212
[58] Field of Search ................ 73/808, 810, 812, 762, 73/787; 116/212; 105/197 R

[56] References Cited

U.S. PATENT DOCUMENTS 2,920,480  1/1960  Haas ....................................... 73/787
3,910,224 10/1975  Thompson et al. ............ 116/212 X Primary Examiner—Jerry W. Myracle
Attorney, Agent, or Firm—Tony T. Shu; Fred P. Kostka; Edward J. Brosius

[57] ABSTRACT

A fatigue detector for detecting potential fatigue failure of a bolster and/or side frames of a railway car truck. The fatigue detector comprises one or more redundant designed members located in areas of critical stress loadings of the truck, wherein the fatigue detectors are structured to fail under a stress loading less than that causing the failure of the bolster and/or side frames in which they are located. The fatigue detector is located in an opening so as to be easily inspected visually to determine its condition and particularly whether or not it has failed.

21 Claims, 6 Drawing Figures

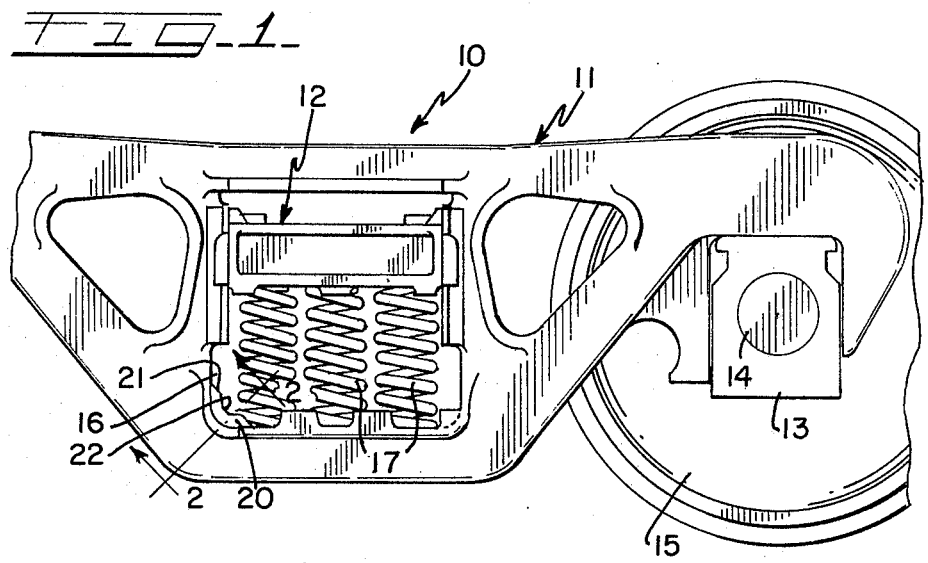
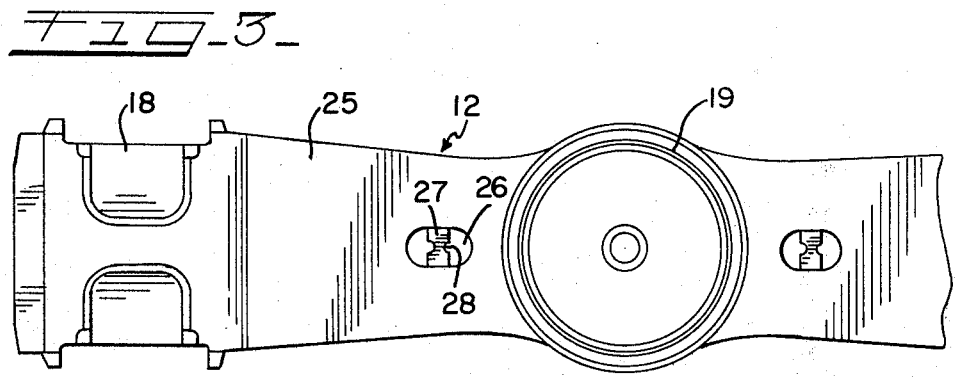

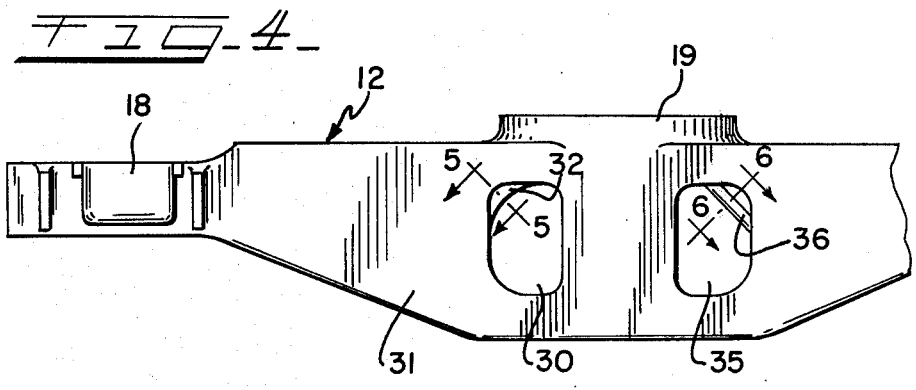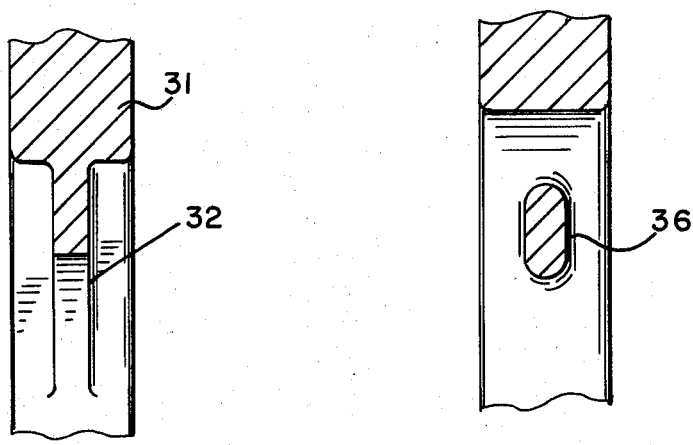

RAILWAY CAR TRUCK FATIGUE DETECTOR

BACKGROUND OF THE INVENTION

1. Field of Invention

This invention relates in general to a fatigue detector for detecting the potential failure of bolster and/or side frame member of a railway car truck, and more particularly to fatigue detectors arranged with respect to areas subjected to highest loading stresses in a railway car truck. The detector is structured to fail upon the application of said loading stresses thereby to warn of potential fatigue failure of said truck.

2. Prior Art

Bolster and side frames of a railway car truck are made by castings which during use are subject to loads which may cause fatigue failure. Accordingly, thorough inspections are made periodically to determine if fatigue cracks in the bolsters and side frames are developing. While the critical areas of fatigue failure in such bolsters and side frames are known, they cover broad areas of the structures which complicate the inspections, thereby requiring the inspector to be quite knowledgeable in the art of truck design. Further, fatigue cracks, especially in the initial stages, are difficult to detect without the use of special equipment, such as Magnaflux, and the like. Such inspections are costly and time consuming.

SUMMARY OF THE INVENTION

The present invention provides an easy method of inspecting railway car trucks to determine the potential fatigue failure of the elements and by obviating the difficulties encountered heretofore. The present invention includes a visually inspectable fatigue detector located on said truck in areas of bolsters or side frames in which fatigue failure, if any, may be likely to occur. The detector is a redundant member which is structured to assume the normal stress loading but to fail by fracture under a loading stress less than that causing the failure of said bolster or side frame upon the application of said critical stresses so as to warn of potential fatigue failure of said truck. Failure of the fatigue detector does not affect the load-carrying ability of the bolster or side frames but merely signals that the fatigue life of the bolster or side frame is approaching its maximum fatigue life. Moreover, the fatigue detector is located so as to be quickly and easily inspected by unskilled personnel, thereby eliminating extensive and costly inspections.

While the fatigue detector of the present invention is especially suitable for use in detecting potential failure of bolsters or side frames of a railway car truck, it will be appreciated that it can also be used to detect the potential failure of drive trucks employed on locomotives.

It is therefore an object of the present invention to provide a fatigue detector for the bolster or side frames of a railway car truck.

A further object of the invention is in the provision of a fatigue detector for a bolster or side frames of a railway car truck in the form of a redundant designed member positioned at a critical area of the bolster or side frame and structured to fail prior to the fatigue failure of the bolster or side frame.

Other objects, features and advantages of the invention will be apparent from the following detailed disclosure, taken in conjunction with the accompanying sheets of drawings.

DESCRIPTION OF THE DRAWINGS

FIG. 1 is a fragmentary side elevational view of the railway car truck and illustrating one form of fatigue detector according to the present invention mounted on the side frame;

FIG. 2 is a greatly enlarged detailed sectional view taken substantially along line 2—2 of FIG. 1;

FIG. 3 is a fragmentary top plan view of a bolster of a railway car truck and which includes a fatigue detector mounted on the bolster;

FIG. 4 is a side elevational view of the bolster illustrated in FIG. 3 and showing alternative forms of fatigue detectors according to the invention;

FIG. 5 is an enlarged detailed sectional view taken substantially along lines 5—5 of FIG. 4; and FIG. 6 is an enlarged detailed sectional view taken substantially along lines 6—6 of FIG. 4.

DESCRIPTION OF THE PREFERRED EMBODIMENT

Referring now to the drawings, and particularly to FIG. 1, a railway car truck 10 in partial fragmentary view is illustrated and includes a side frame 11 supporting a bolster 12. The bolster is supported between a pair of side frames, only one of which is shown. Journals 13 are supported at opposite ends of each of the side frames for receiving axles 14 carrying wheels 15.

Each end of the bolster is guidably received in an opening 16 and resiliently supported relative the side frames by a plurality of springs 17. Thus, the ends 18 of the bolster 12 are received and supported by the side frames 11, while a center plate 19 supports the railway car body (not shown) in the usual manner. Accordingly, it can be appreciated that the load of the car body is transmitted to the bolster through the center plate 19 of the bolster 12, through the ends of the bolster, the springs 17, and to the side frames 11. Finally, the load is transmitted through the journals 13, the axles 14 and the wheels 15 onto the tracks on which the truck 10 will run. The load thereby stresses the bolster and side frames of the truck so as to require periodic inspection to determine whether the bolster or side frames may be subject to failure through fatigue. Heretofore, detection of fatigue cracks have required the use of special equipment.

The present invention eliminates the need for complicated inspections to determine fatigue failure by incorporating redundant designed members into the bolster or side frames which, upon failure, will not affect the load-carrying ability of the truck but merely indicate the maximum fatigue life of the bolster or side frame is being approached. Thus, it is only necessary for an inspector to inspect the fatigue detector to determine the fatigue condition of the bolster or side frames.

It will be recognized that bolsters and side frames of trucks vary in design, whereby the shape, type and size of the fatigue detectors employed with the bolster and side frames may also vary in design. However, the fatigue detector is structured to assume normal stress loading but to fail under a loading stress less than that causing the failure of the bolster or side frames thereby to readily indicate the fatigue life of the bolster or side frames to be nearly exhausted.

An example of a fatigue detector of a side frame is illustrated in FIGS. 1 and 2, wherein a redundant member, indicated by the numeral 20, is located in a corner of the opening 16 of the side frame. As shown, the member 20 is fixedly attached to the structure of the side frame such that it is attached along one side of its entire length at the corner of the opening 16 and defines an exposed or free edge 21. Additionally, the free edge is provided with a notch 22 which provides a specific location of a weakened portion to fail first. Further, the cross-sectional area of the redundant member 20 is substantially less than any of the cross-sectional area of the critical area at the side frame area. The design is such that during stressing of the truck, the redundant member will assume the normal loading but will fail by fracture under a stress loading less than that causing the failure of the side frame 11 at the corner of the opening 16. Accordingly, the redundant member 20 is associated with an opening of the side frame, and its failure will warn of potential failure of the side frame, and it can be readily visually inspected without the need of any special equipment.

A form of a fatigue detector for the upper horizontal panel 25 of a bolster is illustrated in FIG. 3, wherein the panel includes an opening 26. The redundant member used here and indicated by the numeral 27 extends across the opening and is notched at each side at 28. It will be appreciated that the redundant member 27 serves the same purpose as explained in connection with the redundant member 20 of the side frame.

Another form of fatigue detector is illustrated in FIGS. 4 and 5, wherein an opening 30 is provided in a side panel 31 of the bolster 12 and which includes a redundant member 32 associated with one of the corners of the opening 30. It will be appreciated that the opening 30 here is of substantially rectilinear shape as is the opening 16 of the side frame 11. This redundant member is also shown in cross section in FIG. 5, and it can be appreciated that the cross-sectional area of the redundant member 32 is substantially less than the adjacent area of the panel 31. One edge of the redundant member 32 is fixedly attached along its entire length at the corner 30, while the other edge is free or exposed and is accurate in form. The function of this redundant member is the same as those above described.

A still further form of fatigue detector is also illustrated in FIG. 4 in an adjacent opening 35 of the side panel 31 of the bolster. As shown, this redundant member is indicated by the numeral 36 and takes the form in cross section of an oval elongated member fixedly attached at its opposite ends to the sides of the opening 35 and across the corner of the opening. Again, it will be appreciated that the member 36 is of substantially smaller cross section than the area of the bolster panel 31 adjacent thereto, and as in the other redundant members, it would be structured to fail by fracture under a loading stress less than that causing the failure of the adjacent bolster panel 31.

It should be recognized that the design of the fatigue detector will depend upon the type of bolster and/or side frame employed and that it will be used in a critical area known to first experience fatigue failure. Accordingly, by simple inspections of the fatigue detectors, the fatigue condition of the bolster and/or side frames can be readily determined, thereby avoiding untimely costly breakdowns.

It will be understood that modifications and variations may be affected without departing from the scope of the novel concepts of the present invention, but it is understood that this application is to be limited only by the scope of the appended claims.

What is claimed is:

1. A railway car truck comprising a bolster means and a side frame means at the ends of said bolster means, a fatigue detector means located in an area in said truck wherein said bolster means and side frame means are subject to critical stresses, said fatigue detector means being constructed to assume a normal stress loading which may be assumed by said bolster means and said side frame means without fatigue failure but to fail by fracture under a stress loading less than that causing the failure of said bolster means and side frame means upon the application of said critical stress thereby to warn of potential failure of said truck.

2. The invention as described in claim 1 wherein said fatigue detector means is positioned in said bolster means adjacent the area at which said bolster means is subject to fatigue failure.

3. The invention as described in claim 1 wherein said fatigue detector means is positioned in said side frame means adjacent the area at which said side frame means is subject to fatigue failure.

4. The invention as described in claim 1 wherein said fatigue detector means includes a first detector means located in said bolster means and a second detector means located in said side frame means.

5. The invention as described in claim 1 wherein said area includes an opening and said fatigue detector means is located in said opening.

6. A railway truck comprising a bolster means and a side frame means at the ends of said bolster means, a fatigue detector means located in an area in said truck wherein said bolster means and side frame means are subject to critical stresses, said fatigue detector means including a body of which at least a length thereof is of substantially smaller cross-sectional area than that of said area of said truck means whereby said detector serves as a redundant member and simultaneously when fractured serves as a warning of the possibility of failure of said truck means in said area subject to critical stresses.

7. The invention as described in claim 6 wherein said fatigue detector means is located on said truck means so as to be capable of being visually inspected to determine its failure.

8. The invention as described in claim 7 wherein said fatigue detector means is a separate member and is fixedly attached adjacent to said area of said truck means.

9. The invention as described in claim 8 wherein said fatigue detector means is attached adjacent to said area of the opening along one side of its entire length.

10. The invention as described in claim 9 wherein a free edge of said fatigue detector is notched to provide said smaller cross-sectional area.

11. The invention as described in claim 9 wherein said opening is located in said side frame means and said fatigue detector means is connected across a corner thereof.

12. The invention as described in claim 8 wherein said fatigue detector means is elongate and connected at opposite ends to the periphery defining said opening.

13. The invention as described in claim 12 wherein the opposite edges of said fatigue detector means are notched and is located in said opening of the bolster means.

14. The invention as described in claim 12 wherein said opening is located in said side frame means and said fatigue detector means is connected at its opposite ends to the sides and across the corner of said opening.

15. The invention as described in claim 7 wherein said fatigue detector means is integrally formed adjacent to said area of said truck means.

16. The invention as described in claim 15 wherein said fatigue detector means is integrally formed adjacent to said area of the opening along one side of its entire length.

17. The invention as described in claim 16 wherein the free edge of said fatigue detector means is notched to provide said small cross-sectional area.

18. The invention as described in claim 16 wherein said opening is located in said side frame means and the fatigue detector means is connected across a corner thereof.

19. The invention as described in claim 15 wherein said fatigue detector means is elongate and connected at opposite ends to the periphery defining said opening.

20. The invention as described in claim 19 wherein the opposite edges of said fatigue detector means are notched and is located in said opening of the bolster means.

21. The invention as described in claim 18 wherein said opening is located in said side frame means and said fatigue detector means is connected at its opposite ends to the sides and across the corner of said opening.

* * * * *